(12) United States Patent
Masunishi et al.

(10) Patent No.: US 7,744,220 B2
(45) Date of Patent: Jun. 29, 2010

(54) DEFORMABLE MIRROR DEVICE AND APPARATUS FOR OBSERVING RETINA OF EYE USING THE SAME

(75) Inventors: Kei Masunishi, Kawasaki (JP); Akihiro Koga, Tokyo (JP); Ryo Furukawa, Kawasaki (JP); Osamu Nishimura, Kawasaki (JP); Akio Kobayashi, Tokyo (JP); Hiroyuki Kawashima, Tokyo (JP)

(73) Assignees: Kabushiki Kaisha Toshiba, Tokyo (JP); Kabushiki Kaisha Topcon, Tokyo (JP)

(*) Notice: Subject to any disclaimer, the term of this patent is extended or adjusted under 35 U.S.C. 154(b) by 24 days.

(21) Appl. No.: 12/186,142

(22) Filed: Aug. 5, 2008

(65) Prior Publication Data

US 2009/0040462 A1 Feb. 12, 2009

(30) Foreign Application Priority Data

Aug. 8, 2007 (JP) ............................. 2007-206673

(51) Int. Cl.
*A61B 3/10* (2006.01)
*G02B 26/00* (2006.01)
*G02B 5/08* (2006.01)

(52) U.S. Cl. ...................... 351/221; 359/291; 359/295; 359/847

(58) Field of Classification Search ................. 359/290, 359/291, 295, 846, 847; 351/221
See application file for complete search history.

(56) References Cited

U.S. PATENT DOCUMENTS 6,986,587 B2 * 1/2006 Kaneko ..................... 359/847

7,474,455 B2 * 1/2009 Nishio et al. ................ 359/291
7,566,947 B2 * 7/2009 Yang ........................... 257/587

FOREIGN PATENT DOCUMENTS

JP 2-101402 4/1990

OTHER PUBLICATIONS

Masunishi, "Deformable Mirror Device and Apparatus for Observing Retina of Eye Using The Same", U.S. Appl. No. 12/188,018, filed Aug. 7, 2008.

* cited by examiner

*Primary Examiner*—Jack Dinh
(74) *Attorney, Agent, or Firm*—Finnegan, Henderson, Farabow, Garrett & Dunner, L.L.P.

(57) ABSTRACT

A deformable mirror device includes a substrate; a plurality of electrodes provided on the substrate; a spacer disposed on the substrate; a support member disposed above the spacer and having an opening passing through from a first face of the support member facing to the substrate to a second face of the support member opposite from the first face; a deformable electrode film formed below the first face of the support member so as to be opposed to the electrodes with a distance and so as to cover the opening; an insulation film provided between the deformable electrode film and the support member; and a reflection film provided on a face of the deformable electrode film opposite from the electrodes so as to overlap the opening. The electrodes are electrically insulated each other by a plurality of grooves radially extending from a region which includes a position corresponding to a center of the opening.

5 Claims, 7 Drawing Sheets

FIG. 5A
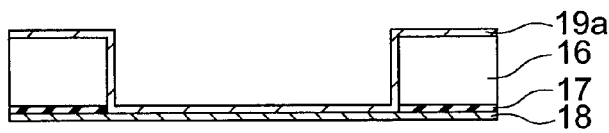
FIG. 5B
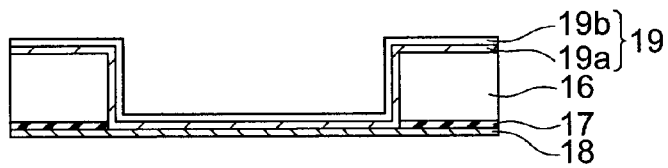
FIG. 5C
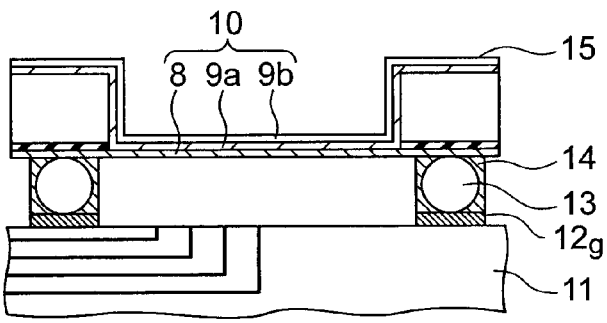
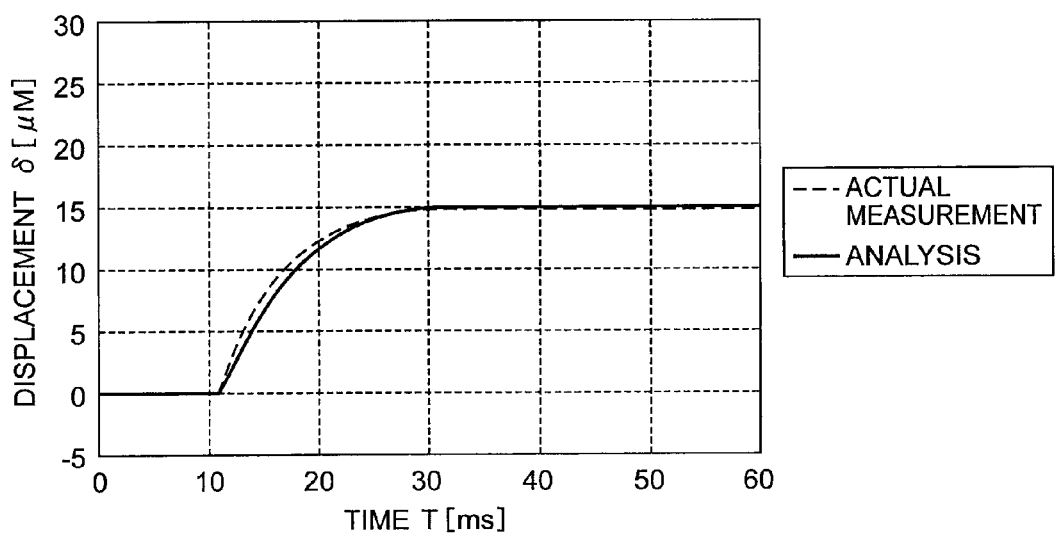
FIG. 6

DEFORMABLE MIRROR DEVICE AND APPARATUS FOR OBSERVING RETINA OF EYE USING THE SAME

CROSS-REFERENCE TO RELATED APPLICATION

This application is based upon and claims the benefit of priority from prior Japanese Patent Application No. 2007-206673 filed on Aug. 8, 2007 in Japan, the entire contents of which are incorporated herein by reference.

BACKGROUND OF THE INVENTION

1. Field of the Invention

The present invention relates to a deformable mirror device having a surface shape deformable by electrostatic force, and an apparatus for observing retina of an eye using such a deformable mirror device.

2. Related Art

In general, the apparatus for observing retina of an eye is an apparatus which irradiates retina of an eye to be examined with illumination light and receives and detects its image through an retina image forming optical system by using an image pickup device (for example, a CCD camera). For detecting and preventing a disease concerning eyes, it is desirable that the detection accuracy and resolution are as high as possible. Since an eyeball is not an ideal lens having no aberration, however, the eyeball has a wavefront aberration which becomes a factor of lowering the detection precision and resolution.

Therefore, a deformable mirror device which can vary its surface shape on the basis of information supplied from a controller is provided between the image pickup device which detects the image of the retina and the retina of the eye to be examined. The image of the retina of the eye to be examined reflected by the deformable mirror device is led to a wavefront sensor (for example, the Shack Hartmann sensor) to detect wavefront aberration. A control device applies voltages to electrodes of the deformable mirror device so as to reduce or eliminate the wavefront aberration on the basis of the detected wavefront aberration and causes an electrostatic force to act upon the deformable mirror to deform it. Owing to this deformation, an image having no wavefront aberration is obtained by the image pickup device.

Deformable mirror devices having a shape deformable by electrostatic sucking force is known (see, for example, FIG. 2 in JP-A 02-101402 (KOKAI)). The deformable mirror device shown in FIG. 2 in JP-A 02-101402 (KOKAI) has a structure consisting of a fixed electrode film 12 formed on an insulative substrate 11, a spacer part 18 having an opening in the center disposed on the fixed electrode film 12, a reflection film 17, a movable electrode film 16 and a $SiO_2$ insulation film 14 stacked on the spacer part 18 so as to cover the opening, and a silicon substrate 13 having an opening in the center disposed on the stacked film. Therefore, the stacked film consisting of the reflection film 17, the movable electrode film 16 and the $SiO_2$ insulation film 14 makes up a membrane part having its peripheral part fixed by the spacer part 18 and the silicon substrate 13, whose central part is deformed by electrostatic force between the fixed electrode 12 and the movable electrode film 16.

For observing retina photoreceptor cells, it is necessary for the deformation of the membrane part to follow eyeball movements such as rotation and translation. Thus, the membrane part is required to have high dynamic characteristics. The deformable mirror device having the shape deformable by electrostatic sucking force has a structure in which the fixed electrode and the membrane part face each other via the spacer part.

Letting F be electrostatic sucking force, $\epsilon$ be the dielectric constant ($=8.85\times10^{-12}$ F/m) of air, S be an electrode area, g be an actual distance (gap) between the fixed electrode and the membrane part, x be a deflection amount of the membrane part, and V be an applied voltage, electrostatic force is given by the following equation (1).

$$F = \frac{1}{2}\varepsilon\frac{S}{(g-x)^2}V^2 \qquad (1)$$

As the distance between the fixed electrode and the membrane part becomes smaller, the electrostatic sucking force becomes larger. If it is desired to drive the deformable mirror device by a low applied voltage, therefore, the distance must be very small.

In the meantime, the squeeze film effect that the time average pressure in a gap over one period becomes higher than that in the neighborhood by vibration in a relative vertical direction of the gap distance between two opposed faces is known. This squeeze film effect occurs between the fixed electrode and the membrane part and exerts a substantial influence upon the vibration characteristics of the membrane part. As a conventional method for reducing the viscosity coefficient C of the vibration system associated with the squeeze film effect, a measure has been taken by sealing the entire deformable mirror device including the fixed electrode and the membrane part in a reduced pressure environment. However, the reduced pressure sealing (reduced pressure packaging) requires a very high cost. and there is a problem that leak of the gas inside the sealing brings about defective products, resulting in a bad cost efficiency.

SUMMARY OF THE INVENTION

The present invention has been made in view of the above state, and an object thereof is to provide a low cost deformable mirror device of an electrostatic drive type capable of improving the dynamic characteristics while maintaining a low driving voltage and an apparatus for observing retina of eye using the same.

A deformable mirror device according to a first aspect of the present invention includes: a substrate; a plurality of electrodes provided on the substrate; a spacer disposed on the substrate; a support member disposed above the spacer and having an opening passing through from a first face of the support member facing to the substrate to a second face of the support member opposite from the first face; a deformable electrode film formed below the first face of the support member so as to be opposed to the electrodes with a distance and so as to cover the opening; an insulation film provided between the deformable electrode film and the support member; and a reflection film provided on a face of the deformable electrode film opposite from the electrodes so as to overlap the opening, wherein the electrodes are electrically insulated each other by a plurality of grooves radially extending from a region which includes a position corresponding to a center of the opening.

An apparatus for observing retina of an eye according to a second aspect of the present invention includes: a retina illumination system configured to illuminate retina of an eye to be examined with illumination light to observe the retina; a compensation optical part configured to include the deformable mirror device according to the first aspect, and correct a reflected image obtained from the retina by the illumination light of the retina illumination system by changing a shape of the deformable mirror device responding to a given correction quantity; a retina image forming optical system configured to receive the retina image corrected by the compensation optical part and form a retina image; and a retina image light receiving part configured to receive the retina image formed by the retina image forming optical system.

BRIEF DESCRIPTION OF THE DRAWINGS

FIGS. 5A to 5C are sectional views showing a manufacturing method of the deformable mirror device according to the first embodiment;

FIG. 6 is a diagram showing measurement and analysis results of response of a membrane part;

DESCRIPTION OF THE EMBODIMENTS

Hereafter, embodiments of the present invention will be described in detail with reference to the drawings.

First Embodiment

Figure 1:
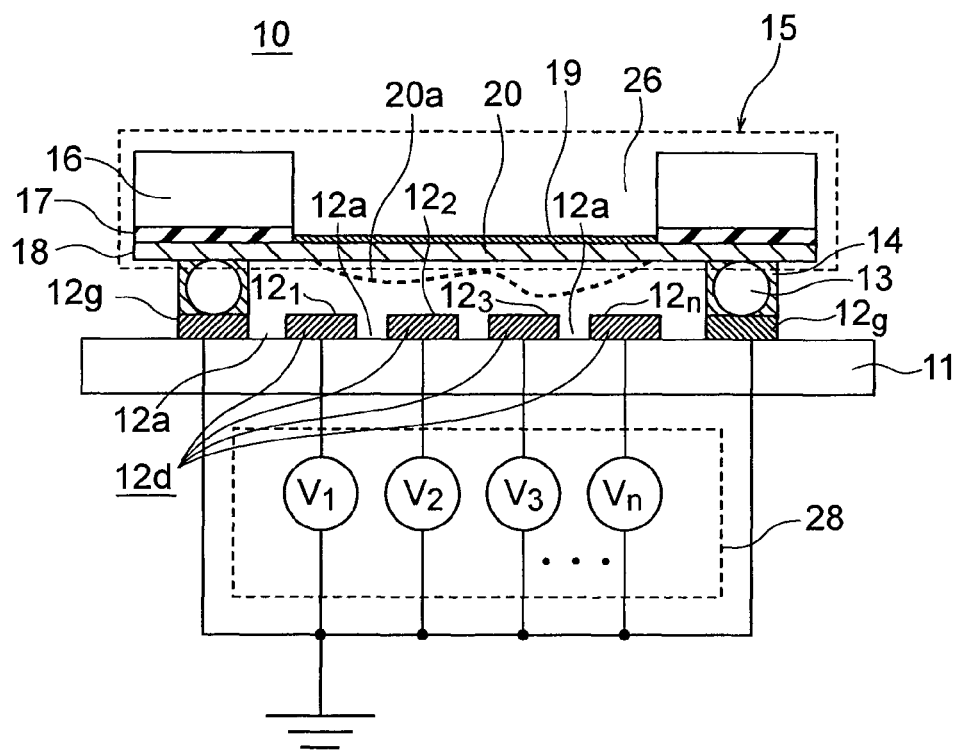
FIG. 1 is a sectional view of a deformable mirror device according to a first embodiment.

A deformable mirror device according to a first embodiment of the present invention is shown in FIG. 1. In a deformable mirror device 10 according to this embodiment, a plurality of electrodes $12_1$ to $12_n$ and $12_g$ having a thickness of, for example, 100 μm are formed on a multi-layered ceramics substrate 11. Furthermore, a drive part 15 is provided on a spacer 13 using, for example, silica balls disposed on the electrodes $12_g$. The electrodes $12_g$ and the drive part 15 are bonded to each other with the spacer 13 interposed therebetween using a conductive adhesive 14. In the drive part 15, a support member 16 which has an opening 26 in the center, substantially constituted by, for example, single crystal silicon and an insulation film substantially constituted by, for example, SiO$_2$ is provided on a face of the support member 16 opposed to the ceramics substrate 11. Furthermore, an electrode film 18 substantially constituted by single crystal silicon doped with impurities is provided on the face of the insulation film 17 opposed to the ceramics substrate 11, covering the opening 16 of the support member 16 and facing to the electrodes $12_1$ to $12_n$. The electrode film 18 is supported by the support member 16 via the insulation film 17. Furthermore, a reflection film 19 (reflection part) is provided in a region in the surface of the electrode film 18 facing to the electrodes $12_1$ to $12_n$ where the electrode film 18 and the opening of the support member 16 overlaps. The electrode film 18 and the reflection film 19 constitute a deformable membrane part 20.

The distance (gap) between surfaces of the electrodes $12_1$ to $12_n$ and $12_g$ and the bottom face of the drive part 15 is adjusted by the spacer 13 and the electrodes $12_g$. At that time, the electrodes $12_g$ serve as grounding electrodes. As a matter of course, a structure in which the spacer 13 for adjusting the gap and the electrodes $12_g$ for grounding the drive part 15 are provided in different positions may be used. Voltages $V_1$ to $V_n$ generated by a voltage generation part 28 are applied to the electrodes $12_1$ to $12_n$, respectively. As a result of the application of the voltages $V_1$ to $V_n$ to the electrodes $12_1$ to $12_n$, electrostatic sucking force acts upon the membrane part 20 and deforms it. The deformed membrane part is denoted by a symbol 20a.

Figure 2:
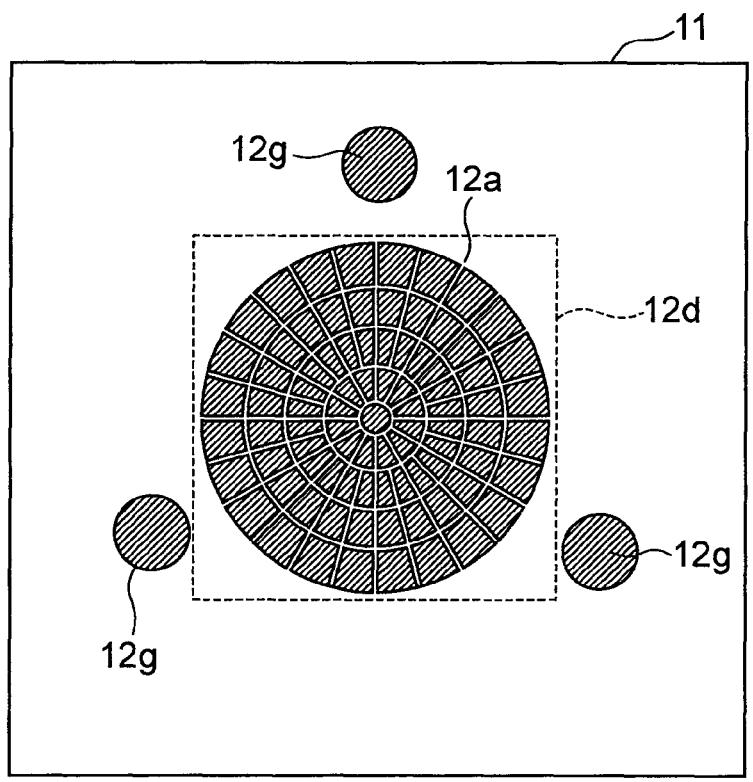
FIG. 2 is a top view showing a shape of an electrode divided into a plurality of parts according to the first embodiment.

Disposition of the drive electrode $12_d$ and the ground electrodes $12_g$ is shown in FIG. 2. The drive electrode $12_d$ disposed so as to be opposed to the membrane part 20 has a structure including a plurality of electrodes $12_1$ to $12_n$ provided by dividing the drive electrode concentrically around a position facing to a center position of the membrane part 20 with grooves 12a, dividing it periodically and radially, and electrically insulating the resulting electrodes. The ground electrodes $12_g$ are disposed outside the outermost circumference of the drive electrode $12_d$. In a region located outside the outermost circumference part of the drive electrode $12_d$ except the ground electrodes $12_g$, the surface level becomes approximately 100 μm lower than that of the electrodes $12_1$ to $12_n$, and the surface of the multi-layered ceramics substrate 11 is exposed. Therefore, the distance between surfaces of the electrodes $12_1$ to $12_n$ and $12_g$ and the bottom face of the drive part 15 differs from the distance between bottom faces of the grooves 12a located between the electrodes and the bottom face of the drive part 15 by the film thickness of the electrodes, i.e., approximately 100 μm. As recognized from FIG. 2, one of the drive electrodes is located in a position facing to the center position of the membrane part 20 so as to be able to deform the membrane part 20 at its central position.

Figure 3A:
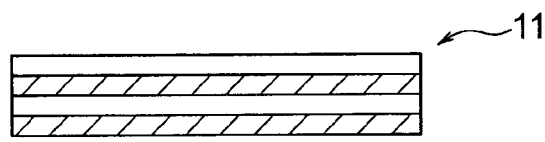
FIGS. 3A to 3E are sectional views showing manufacturing processes of the electrode according to the first embodiment.
Figure 3B:
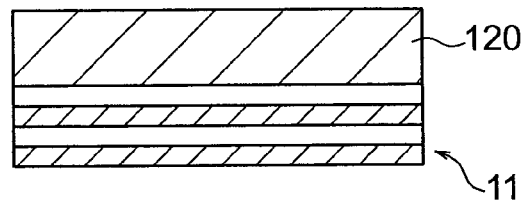
Figure 3C:
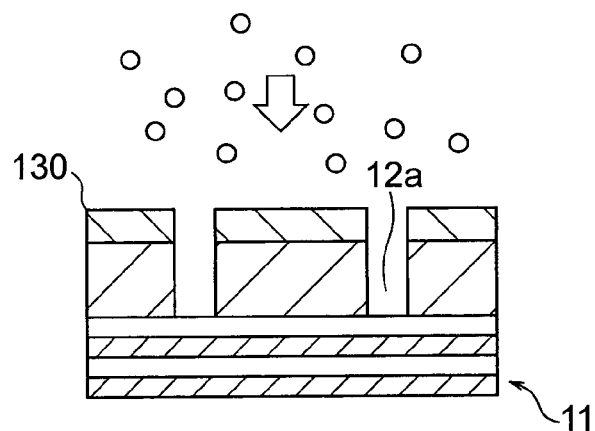
Figure 3D:
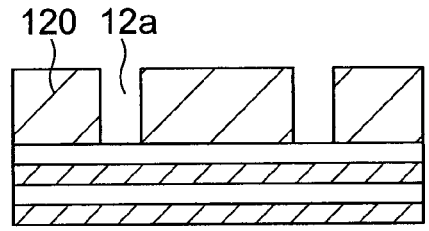
Figure 3E:
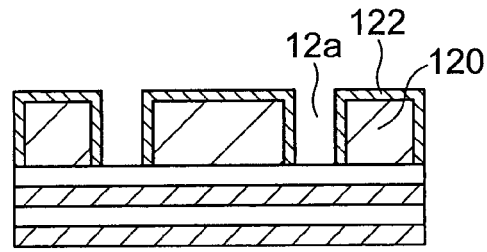

A method for forming the drive electrode $12_d$ and the grounding electrodes $12_g$ will now be described with reference to FIGS. 3A to 3E. First, an underlayer (not illustrated) including, for example, Ni as its principal element is formed on the multi-layered ceramics substrate 1 as shown in FIG. 3A. A Cu layer 120 including a conductive material such as Cu as its principal element is formed on the underlayer so as to obtain a thickness of approximately 100 μm (FIG. 3B). Subsequently, a mask 130 is formed on the Cu layer 120, and then grooves 12a are formed on the Cu layer 120 by sandblasting to divide the Cu layer 120 into a plurality of parts (FIG. 3C). Furthermore, the mask 130 is removed, and then the surface of the Cu layer 120 divided into a plurality of parts is polished and planarized (FIG. 3D). Subsequently, an underlayer (not illustrated) including Ni as its principal element is formed on the surface of the Cu layer 120 divided into parts, by Ni plating. Thereafter, an Au layer 122 is coated on a surface of the underlying layer by gold plating. By such fabrication process, a plurality of electrodes $12_1$ to $12_n$ and $12_g$ divided by the grooves 12a are formed. As a result, the deep grooves 12a can be formed between electrodes while maintaining the parallelism among surfaces of the electrodes $12_1$ to $12_n$ and $12_g$. In other words, the electrodes $12_1$ to $12_n$ and $12_g$ have a four-layer structure represented as "Ni layer (underlayer)/Cu layer/Ni layer (plating underlayer)/Au layer."

A method for manufacturing the deformable mirror device according to the present embodiment will now be described with reference to FIGS. 4A to 5C.

Figure 4A:
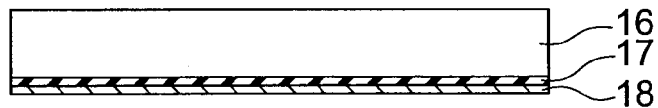
FIGS. 4A to 4E are sectional views showing a manufacturing method of the deformable mirror device according to the first embodiment.

First, a SOI (Silicon On Insulator) substrate 16, 17 and 18 is prepared as shown in FIG. 4A. Typically, the SOI substrate is prepared as hereinafter described. A single crystal Si wafer is prepared, and a $SiO_2$ film is formed on the entire wafer (both the obverse and reverse) by using a thermal oxidation furnace or the like (the film thickness on the obverse is the same as that on the reverse). Another single crystal Si wafer is subsequently bonded to the first single crystal Si wafer by interposing one of the $SiO_2$ films therebetween. After the bonding, one of the bonded single crystal Si wafers is made thin by a polishing process until a desired thickness is attained. Thereafter, an $SiO_2$ films which has not been used as a bonding surface is removed. As a result, an SOI substrate 16, 17 and 18 having a "the single crystal Si layer (support member) 16/the $SiO_2$ film (insulation film) 17/the single crystal Si layer (electrode film) 18" three-layer structure is obtained. In the meantime, high concentration impurities have been introduced into the single crystal Si layer 18, and it has been an electrically conductive film.

Figure 4B:
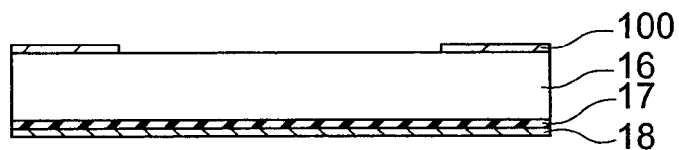

Subsequently, as shown in FIG. 4B, the single crystal Si layer 16 is coated by a photoresist, and exposure and development is conducted on the photoresist. As a result, a resist pattern 100 having an opening in the center is formed.

Figure 4C:
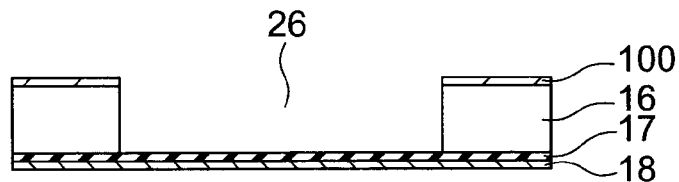

Subsequently, an opening 26 is formed in the center of the single crystal Si layer 16 by dry etching using deep-RIE (Reactive Ion Etching) with the resist pattern 100 used as a mask (see FIG. 4C). The etching process for the single crystal Si layer 16 uses the $SiO_2$ film 17 as the etching stop. In other words, the etching is finished when the $SiO_2$ film 17 is exposed.

Figure 4D:
Figure 4E:

Subsequently, the resist pattern 100 is removed (see FIG. 4D). Thereafter, the substrate is immersed in, for example, diluted fluoric acid or ammonium fluoride to remove the $SiO_2$ film 17 existing on the bottom of the opening 26 (FIG. 4E).

Subsequently, in order to obtain optical reflection characteristics, a metal thin film 19a substantially constituted by Al is formed by, for example, evaporation so as to cover at least the bottom of the opening 26 (FIG. 5A). Subsequently, a $SiO_2$ thin film 19b is formed by, for example, evaporation as a protection film functioning as a measure against scratches and dirt (FIG. 5B). In the present embodiment, the metal thin film 19a and the $SiO_2$ thin film 19b are formed also on the side face of the opening 26 and the single crystal Si layer 16. The metal thin film 19a and the $SiO_2$ thin film 19b constitute the reflection film 19. Thus, the drive part 15 of the deformable mirror device is completed. In the meantime, the shape (planar shape) of the drive part 15 is, for example, a square.

Subsequently, as shown in FIG. 5C, the drive part 15 is bonded to the ceramics substrate 11 having the electrodes $12_1$ to $12_n$ and $12_g$ formed thereon, via the spacer 13 by using the adhesive 14 to complete the deformable mirror device.

Hereinafter, it will be described that the viscosity coefficient C in the vibration system can be reduced by employing a structure in which the electrodes $12_1$ to $12_n$ and $12_g$ are formed by the grooves 12a as in the present embodiment.

Figure 7:
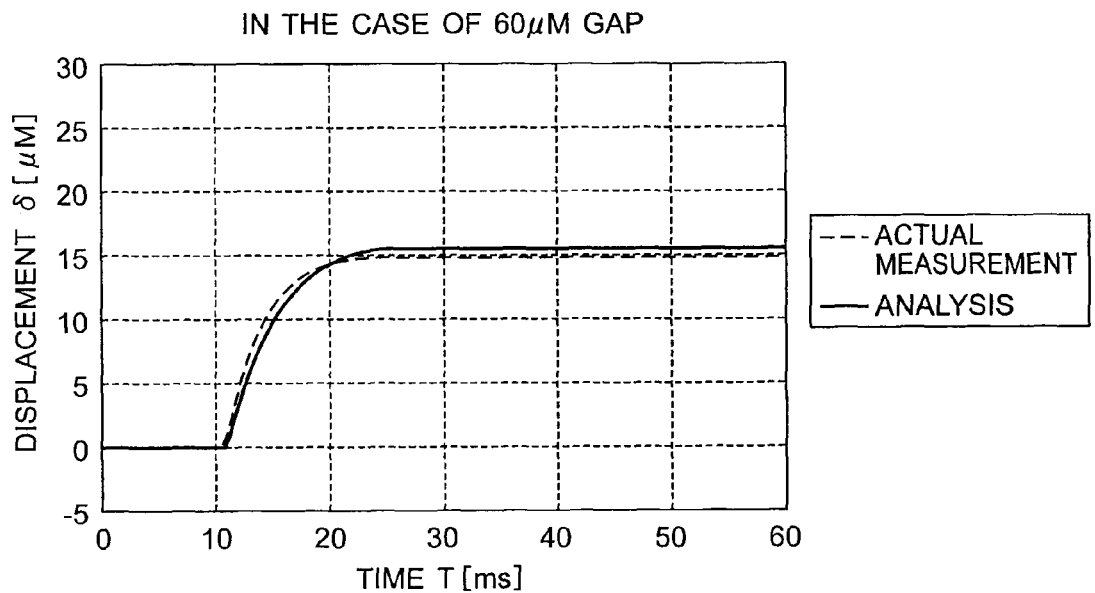
FIG. 7 is a diagram showing measurement and analysis results of response of a membrane part.

Deformable mirror devices prepared with 50 μm and 60 μm distance (gap) between the surfaces of the electrodes $12_1$ to $12_n$ and $12_g$ and the bottom faces of the membrane part 20 and the drive part 15 when no voltage is applied to the electrodes $12_1$ to $12_n$ and $12_g$ are fabricated. Results obtained by measuring and analyzing the response of the deformation of the respective membrane parts 20 are shown in FIG. 6 and FIG. 7. However, the fabricated deformable mirror device has a configuration in which the depth of the grooves 12a between the electrodes $12_1$ to $12_n$ and $12_g$ are very shallow and the grooves 12a do not arrive at the top face of the ceramics substrate 11, or a configuration in which, unlike the present embodiment, walls having the same height as that of the electrodes exist outside the outermost circumference electrodes and restrain in- and out-flows of fluid between gaps even if grooves arriving at the top face of the ceramics substrate 11 are formed. As recognized from FIGS. 6 and 7, the response of the deformation of the membrane part 20 is better when the gap is 60 μm as compared with when the gap is 50 μm.

Figure 8:
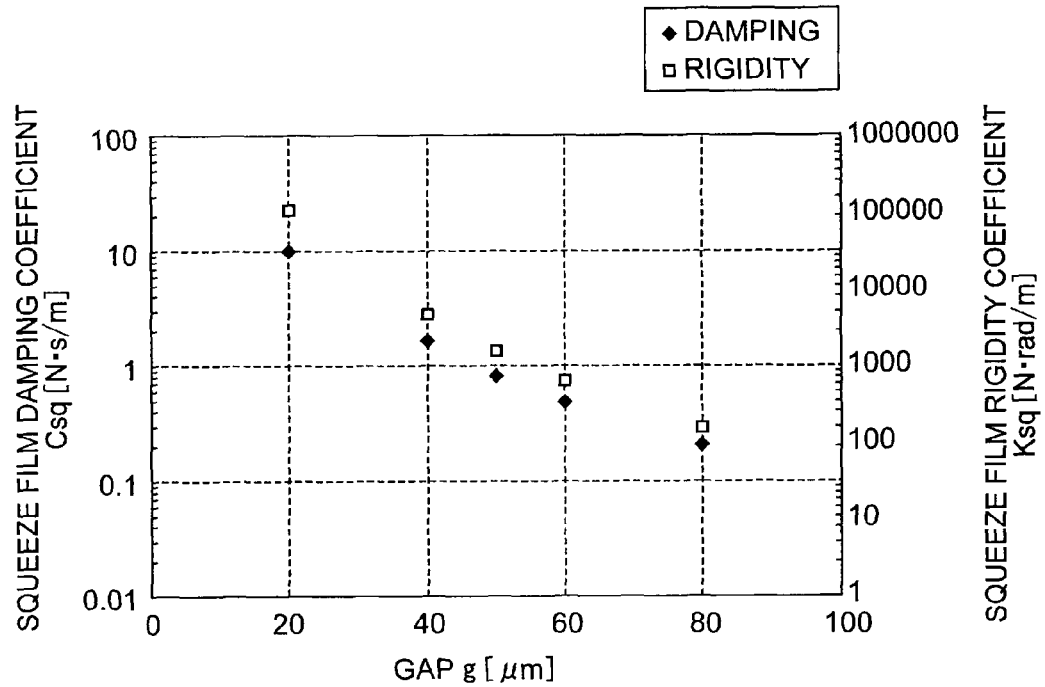
FIG. 8 is a diagram showing vibration characteristics of the membrane part.

Further, FIG. 8 shows a result obtained by analyzing changes in the squeeze film damping coefficient (causing degradation in response) and the squeeze film rigidity coefficient when the distance (gap) between the surfaces of the electrodes $12_1$ to $12_n$ and $12_g$ and the bottom faces of the membrane part 20 and the drive part 15 is changed. As recognized from FIG. 8, the squeeze film damping coefficient and the squeeze film rigidity coefficient decrease as the distance (gap) between the surfaces of the electrodes $12_1$ to $12_n$ and $12_g$ and the bottom faces of the membrane part 20 and the drive part 15 becomes larger.

For the fluid, forming deep grooves 12a arriving at the top face of the substrate 11 radially between the electrodes and exposing the top face of the multi-layered ceramics substrate 11 in the region located outside the electrodes in the outermost circumference part becomes equivalent to expanding the distance (gap) from the bottom faces of the membrane part 20 and the drive part 15. Therefore, the squeeze film damping coefficient reduces. As a result, improvement of the response of the membrane part 20 can be expected. Moreover, since the electrostatic sucking force acts depending upon the actual distance (gap) between the surfaces of the electrodes $12_1$ to $12_n$ and $12_g$ and the bottom faces of the membrane part 20 and the drive part 15, it is not necessary to increase the drive voltage.

In the present embodiment, the grooves 12a formed radially are disposed at an equal angle interval. Alternatively, the grooves 12a may not be at an equal angle interval.

As heretofore described, deep grooves 12a arriving at the surface of the substrate 11 are formed radially between the electrodes, and the height in the region located outside the electrodes in the outermost circumference part is made lower than the electrodes $12_1$ to $12_n$ and $12_g$. As a result, improvement of the response of the membrane part 20 can be expected, and the need to increase the drive voltage can also be eliminated.

If not only the grooves 12a between the electrodes are formed radially, but also a plurality of grooves 12a are concentrically formed, it becomes possible for fluid (air) which cannot otherwise flow to the outside via one of the radially formed grooves 12a to flow into other radially formed grooves 12a via a groove 12a formed concentrically. Accordingly, the squeeze film damping coefficient further reduces. As a result, further improvement of the response of the membrane part 20 can be expected.

According to the present embodiment, therefore, the dynamic characteristics can be improved at a low cost while maintaining low voltage drive.

Second Embodiment

Figure 9:
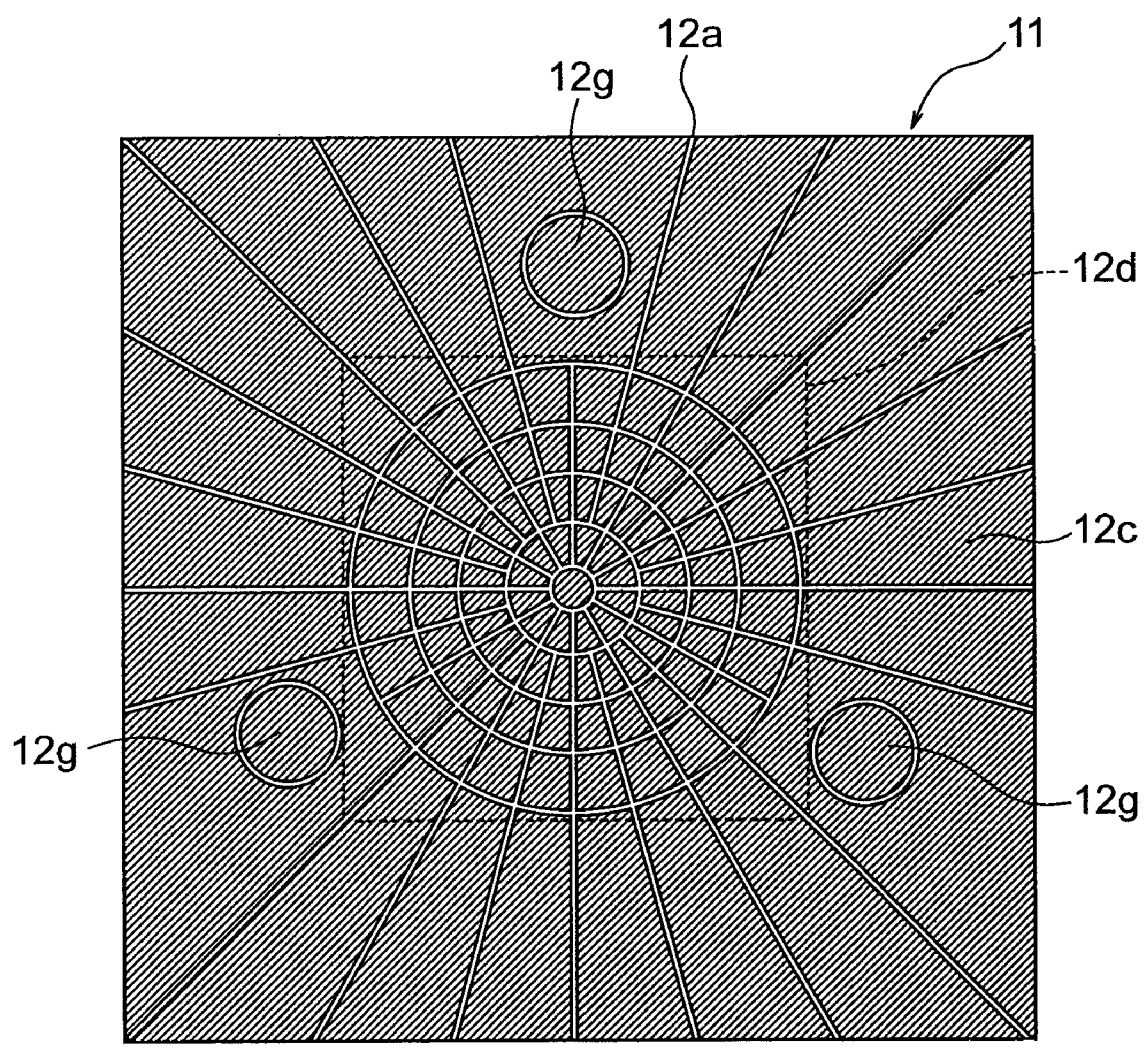
FIG. 9 is a top view showing a shape of an electrode according to a second embodiment.

A deformable mirror device according to a second embodiment of the present invention will now be described. The deformable mirror device according to the present embodiment has a configuration obtained from the deformable mirror device according to the first embodiment by leaving an electrode material 12c having the same height as the drive electrodes $12_1$ to $12_n$ in the region located outside the electrodes in the outermost circumference part of the drive electrodes $12_1$ to $12_n$, and extending the grooves $12a$ radially in order to form the drive electrodes $12_1$ to $12_n$ (FIG. 9).

For fluid, employing such a structure is equivalent to increasing the distance (gap) from the bottom faces of the membrane part 20 and the drive part 15. Accordingly, the squeeze film damping coefficient reduces. As a result, improvement of the response of the membrane part 20 can be expected. Moreover, since the electrostatic sucking force acts according to the actual distance (gap) between the surfaces of the electrodes $12_1$ to $12_n$ and $12_g$ and the bottom faces of the membrane part 20 and the drive part 15, it is not necessary to increase the drive voltage.

As heretofore described, according to the present embodiment, the grooves $12a$ between the electrodes are formed radially and periodically, and the grooves $12a$ are extended to the outside of the position where the membrane part 20 and the drive part 15 face. As a result, improvement of the response of the membrane part 20 can be expected, and the need to increase the drive voltage can also be eliminated.

According to the present embodiment, therefore, the dynamic characteristics can be improved at a low cost while maintaining low voltage drive.

Third Embodiment

An apparatus for observing retina of an eye according to a third embodiment of the present invention will now be described.

Figure 10:
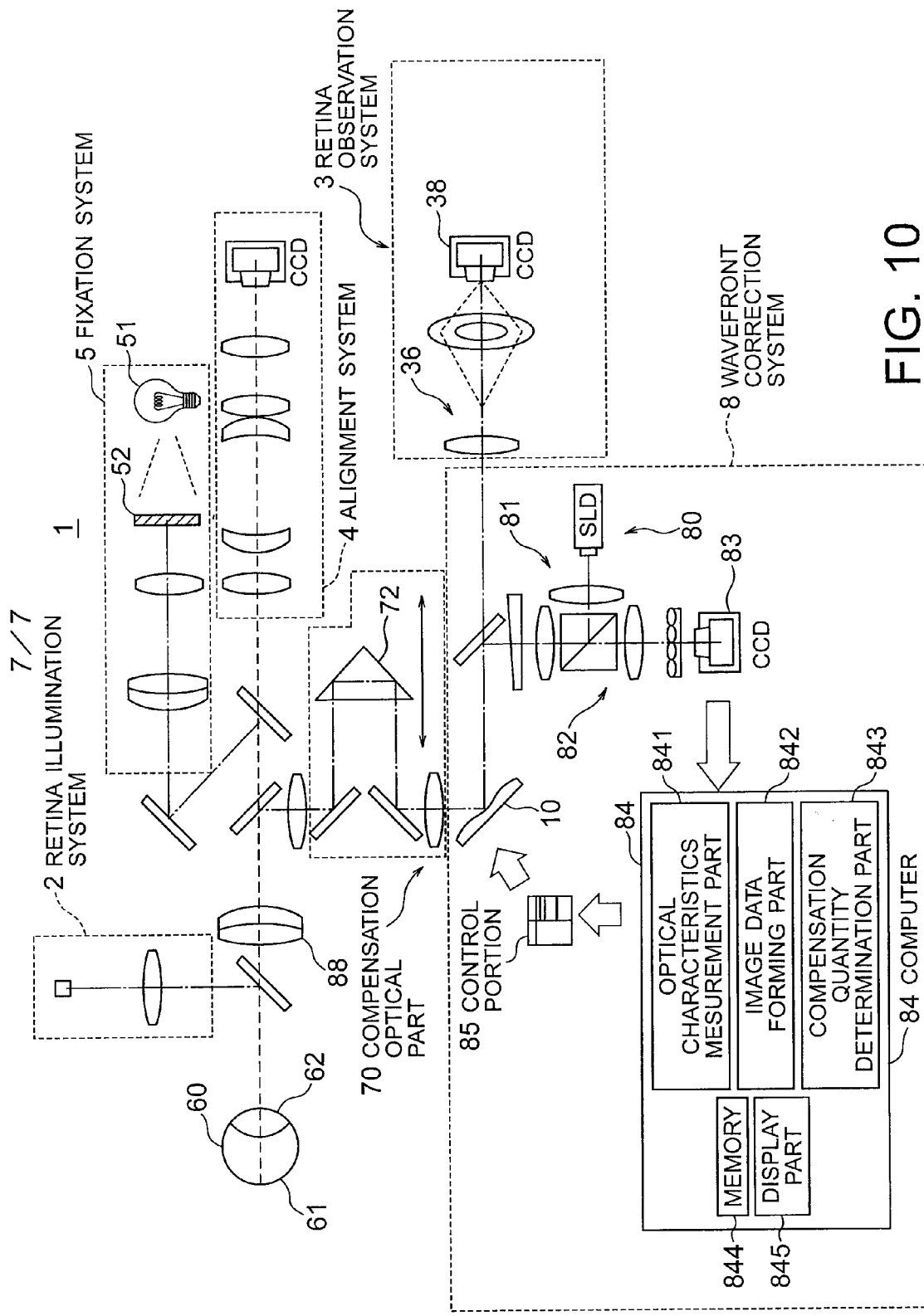
FIG. 10 is a block diagram showing an apparatus for observing retina of an eye according to a third embodiment of the present invention.

The apparatus for observing retina of an eye according to the present embodiment includes the deformable mirror device 10 according to any one of the first and second embodiments. A system of the apparatus for observing retina of an eye according to the present embodiment is schematically shown in FIG. 10. An apparatus for observing retina of an eye 1 according to the present embodiment includes a wavefront correction system 8, a retina illumination system 2, a retina observation system 3, an alignment system 4, a fixation system 5 and a compensation optical part 70. The wavefront correction system 8 includes a wavefront measurement system 80, a computer 84 and a control part 85. The wavefront measurement system 80 includes a point image projection optical system 81, a point image receiving optical system 82 and a point image receiving part 83 (CCD). The computer 84 includes an optical characteristics measurement part 841, an image data forming part 842, a compensation quantity determination part 843, a memory 844 and a display part 845.

The retina illumination system 2 includes a second light source part, a condenser lens and a beam splitter. The retina illumination system 2 is provided to illuminate a predetermined region on retina of an eye to be examined with a second luminous flux emitted from the second light source part. The retina observation system 3 includes a retina image forming optical system 36 and a retina image receiving part 38 (CCD). The retina image forming optical system 36 includes, for example, an afocal lens 88, the compensation optical part 70, a condenser lens and a beam splitter. The retina image forming optical system 36 guides light reflected by a retina 61 to the retina image receiving portion 38 via the compensation optical part 70. The compensation optical part 70 includes the deformable mirror device 10 which compensates aberration of measured light and a moving prism and a spherical lens which move in the optical axis direction and compensate a spherical component. The compensation optical part 70 is disposed between the point projection optical system 81 and the retina image forming optical system 36, and the compensation optical portion 70 compensates, for example, aberration of the returning luminous flux reflected by the eye 60 to be examined.

The alignment system 4 includes a condenser lens and an alignment light receiving portion, and guides returning luminous flux emitted from the light source part and reflected by cornea 62 of the eye 60 to be examined. The fixation system 5 includes an optical path which projects a fixation point for fixation or fogging of the eye 60 to be examined, a third light source part 51, a fixation table 52 and relay lenses. The fixation table 52 can be projected to the retina 61 using luminous flux emitted from the third light source portion 51, which makes the eye 60 to be examined observe an image of the fixation index 52.

The optical characteristics measurement part 841 determines optical characteristics including higher order aberration of the eye 60 to be examined on the basis of an output from the point light receiving part 83. The image data forming part 842 simulates how the fixation index appears on the basis of optical characteristics and calculates simulation image data or examined eye data such as the MTF showing how the fixation appears. The memory 844 stores a plurality of voltage change templates for adjusting the deformable mirror 10. The compensation quantity determination part 843 selects a voltage change template stored in the memory 844, determines a correction quantity of the deformable mirror 10 on the basis of the selected voltage change template, and outputs the correction amount to the control part 85. The control part 85 deforms the deformable mirror device 10 on the basis of an output from the compensation quantity determination portion 843.

The apparatus for observing retina of an eye according to the present embodiment has effects described hereinafter. Reflected light from the retina of the eye 60 to be examined contains aberration because the eye optical system is not ideal, and a clear retina image is not obtained. In the current retina camera, therefore, cylinder components (Zernike (2, ±2) components) are corrected by inserting a correction cylinder lens in the optical path. A distinct retina image with sufficient aberration correction can not be obtained due to a restriction that the refraction degree intervals of the cylinder lens (for example, 3 D (diopter) intervals) is constant. The optical distortion can be corrected by using the deformable mirror device 10. If the distance between the membrane part and the electrodes is made large and the deformable mirror device 10 is driven with a high drive voltage, a large aberration quantity capable of covering the refraction degree interval of the cylinder lens can be corrected. Furthermore, a complicated aberration can be corrected by increasing the number of electrodes under the membrane part.

According to the embodiments of the present invention, it is possible to improve the dynamic characteristics at low cost while maintaining the low voltage drive as heretofore described.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concepts as defined by the appended claims and their equivalents.

What is claimed is:

1. An apparatus for observing retina of an eye comprising:
   a retina illumination system configured to illuminate retina of an eye to be examined with illumination light to observe the retina;

a compensation optical part configured to comprise a deformable mirror device, and correct a reflected image obtained from the retina by the illumination light of the retina illumination system by changing a shape of the deformable mirror device responding to a given correction quantity;

a retina image forming optical system configured to receive the retina image corrected by the compensation optical part and form a retina image; and a retina image light receiving part configured to receive the retina image formed by the retina image forming optical system, wherein the deformable mirror device comprises:
  a substrate;
  a plurality of electrodes provided on the substrate;
  a spacer disposed on the substrate;
  a support member disposed above the spacer and having an opening passing through from a first face of the support member facing to the substrate to a second face of the support member opposite from the first face;
  a deformable electrode film formed below the first face of the support member so as to be opposed to the electrodes with a distance and so as to cover the opening;
  an insulation film provided between the deformable electrode film and the support member; and
  a reflection film provided on a face of the deformable electrode film opposite from the electrodes so as to overlap the opening,
  the electrodes being electrically insulated from each other by a plurality of grooves radially extending from a region which includes a position corresponding to a center of the opening.

2. The apparatus according to claim 1, wherein the electrodes are electrically insulated from each other by the grooves which extend from the center of the opening at an equal angle interval.

3. The apparatus according to claim 1, wherein the electrodes are electrically insulated from each other by a plurality of grooves disposed concentrically around the position corresponding to the center of the opening.

4. The apparatus according to claim 1, wherein
a film of the same material as that of the electrodes is formed in a region on the substrate located outside an outermost circumference of the electrodes, and
the film is divided by radially extending grooves.

5. The apparatus according to claim 1, wherein
the support member comprises silicon,
the insulation film comprises silicon oxide, and
the deformable electrode film comprises a silicon film doped with impurities.

* * * * *